(12) United States Patent
Kim et al.

(10) Patent No.: US 11,173,304 B2
(45) Date of Patent: Nov. 16, 2021

(54) THREE-DIMENSIONAL ELECTRODE DEVICE AND METHOD FOR MANUFACTURING THE SAME

(71) Applicant: DAEGU GYEONGBUK INSTITUTE OF SCIENCE & TECHNOLOGY, Daegu (KR)

(72) Inventors: So Hee Kim, Daegu (KR); Hee Won Seo, Gyeonggi-do (KR)

(73) Assignee: DAEGU GYEONGBUK INSTITUTE OF SCIENCE & TECHNOLOGY, Daegu (KR)

( * ) Notice: Subject to any disclaimer, the term of this patent is extended or adjusted under 35 U.S.C. 154(b) by 81 days.

(21) Appl. No.: 16/376,316

(22) Filed: Apr. 5, 2019

(65) Prior Publication Data
US 2019/0308019 A1    Oct. 10, 2019

(30) Foreign Application Priority Data

Apr. 5, 2018  (KR) .......................... 10-2018-0039956

(51) Int. Cl.
*A61N 1/36*    (2006.01)
*A61N 1/05*    (2006.01)
(Continued)

(52) U.S. Cl.
CPC ....... *A61N 1/36046* (2013.01); *A61N 1/0543* (2013.01)

(58) Field of Classification Search
CPC .......................... A61N 1/0543; A61N 1/36046
(Continued)

(56) References Cited

U.S. PATENT DOCUMENTS 4,628,933 A * 12/1986 Michelson ................ A61F 2/14
607/53
6,393,327 B1 * 5/2002 Scribner .............. A61N 1/0543
607/54
(Continued)

FOREIGN PATENT DOCUMENTS

KR    10-2003-0035738    5/2003
KR    10-2012-0108884    10/2012
(Continued)

OTHER PUBLICATIONS

Byun et al., Fabrication of a flexible penetrating microelectrode array for use on curved surfaces of neural tissues, J. Micromech. Microeng. 23: 125010 (14pp) (Year: 2013).*

(Continued)

*Primary Examiner* — Mallika D Fairchild
*Assistant Examiner* — Vynn V Huh
(74) *Attorney, Agent, or Firm* — Lex IP Meister, PLLC

(57) ABSTRACT

A three-dimensional electrode device and a method for manufacturing the same are disclosed. A three-dimensional electrode device as disclosed can be in close contact with target cells in a retina without damaging the retina to apply electrical stimulation to the retina. The three-dimensional electrode device can include a board prepared to be inserted into a photoreceptor layer in an eyeball and formed of a transparent material; and a plurality of electrodes formed on the board and configured to stimulate a retina. The board can be prepared to be deformed corresponding to a shape of the retina and configured to make the electrodes be in close contact with the retina.

11 Claims, 18 Drawing Sheets

(51) Int. Cl.
    *A61B 3/10*     (2006.01)
    *H01B 13/00*     (2006.01)
    *H01B 13/06*     (2006.01)

(58) Field of Classification Search
    USPC ........................................ 607/1–95, 115–156
    See application file for complete search history.

(56) References Cited

U.S. PATENT DOCUMENTS

| | | |
|---|---|---|
| 7,079,900 B2 | 7/2006 | Greenberg et al. |
| 9,345,568 B2 | 5/2016 | Cho et al. |
| 2013/0310933 A1 | 11/2013 | Cho |
| 2015/0209586 A1* | 7/2015 | Silva .................. A61N 1/36046 |
| | | 607/54 |
| 2019/0209833 A1* | 7/2019 | Kim .......................... A61F 9/08 |
| 2020/0147385 A1* | 5/2020 | Deterre .............. A61N 1/36046 |

FOREIGN PATENT DOCUMENTS

| | | |
|---|---|---|
| KR | 10-2018-0008929 | 1/2018 |
| WO | 2012-058477 | 5/2012 |

OTHER PUBLICATIONS

KIPO, Notice of Allowance of KR 10-2018-0039956 dated Jul. 27, 2020.

\* cited by examiner (a)  (b)

(a)  (b)

THREE-DIMENSIONAL ELECTRODE DEVICE AND METHOD FOR MANUFACTURING THE SAME

BACKGROUND OF THE INVENTION

Field of the Invention

The present invention relates to a three-dimensional electrode device and a method for manufacturing the same and more particularly, to a three-dimensional electrode device which can be in close contact with the target cells in the retina without damaging the retina to apply electrical stimulation to the retina and a method for manufacturing the same.

Description of the Related Art

In general, an electrical retinal stimulator is configured to form an artificial retina by cutting an external membrane, inserting an electrode device into a slit and making the inserted electrode device in close contact with the target cells in the retina.

Further, it has been difficult for a conventional electrode device to closely contact with the retina along the curve of the retina due to its thickness. Therefore, the electrodes of the electrode device cannot be in close contact with the target cells in the retina due to different eyeball sizes or the curve of the retina and thus can be easily detached from the retina when the head moves during surgery or during activities.

If the electrodes cannot be in close contact with the target cells in the retina, it is impossible to accurately apply electrical stimulation to a desired spot.

Therefore, conventionally, the electrode device has been attached to the retina and then fixed using an additional device to suppress the electrode device not to be moved and easily detached from the retina. However, it is uneconomical to attach the electrode device using the additional device because it requires increased surgical time and manufacturing cost, and it is impossible to stably attach the electrode device for a long time.

Further, U.S. Pat. No. 7,079,900 (hereafter, referred to as "conventional technology") discloses a technology of fixing an electrode device to the retina without an additional device. However, the conventional technology runs a risk of damaging the retinal cells because the electrodes fixed to the retina is pointed.

CITATION LIST

Patent Literature

Patent Literature 1: U.S. Pat. No. 7,079,900

SUMMARY OF THE INVENTION

An object of the present invention to solve the above-described problems is to provide a three-dimensional electrode device which can be in close contact with the target cells in the retina without damaging the retina to apply electrical stimulation to the retina and a method for manufacturing the same.

However, problems to be solved by the present invention are not limited to the above-described problems. Although not described herein, other problems to be solved by the present invention can be clearly understood by a person with ordinary skill in the art from the following descriptions.

To achieve the above-described object, the present invention provides a three-dimensional electrode device, including: a flexible board prepared to be inserted into the photoreceptor layer of the retina in an eyeball and formed of a transparent material; and a plurality of electrodes formed on the board and configured to stimulate the retina, and the board is prepared to be deformed corresponding to a shape of the retina and configured to make the electrodes be in close contact with the retina.

In an exemplary embodiment of the present invention, the electrodes may be prepared to have curved surfaces or flat surfaces to be attached to the retina and thus may suppress damage to the retina when the electrodes are in close contact with the target cells in the retina.

In an exemplary embodiment of the present invention, the electrodes may be arranged in a lattice shape or hexagonal shape or arranged with alternating rows or columns on the board.

In an exemplary embodiment of the present invention, the three-dimensional electrode device may further include: a circuit prepared to be further combined with a lower part of the board; and a photo diode prepared on an upper side of the circuit and one side of the electrodes and connected to the electrodes, and the photo diode may convert light energy incident through the board into electric energy to enable the electrodes to stimulate the retina or measure an electrical signal from the retina.

To achieve the above-described object, the present invention provides a method for manufacturing a three-dimensional electrode device, including: a process a) of depositing a metal layer on a wafer and patterning the metal layer into a predetermined shape; a process b) of forming a processing hole in the wafer; a process c) of forming a board in the processing hole; a process d) of cutting the wafer to form an electrode; a process e) of forming a deposition layer on an end portion of the electrode to be attached to a retina; and a process f) of forming an insulating layer on external surfaces of the electrode and the board except a surface of the deposition layer, and the board is prepared to be deformed corresponding to a shape of the retina and configured to make the electrodes be in close contact with the retina.

In an exemplary embodiment of the present invention, in the process a), the wafer is formed of silicon and the metal layer is formed of gold (Au) and titanium (Ti) or the gold and chromium (Cr), and the titanium or the chromium enhances an attachment between the gold and the wafer formed of the silicon.

In an exemplary embodiment of the present invention, the process b) may include: a process b1) of forming a photosensitive mask layer of photoresist on the metal layer; a process b2) of performing deep reactive ion etching to the wafer; and a process b3) of removing the photosensitive mask layer.

In an exemplary embodiment of the present invention, the process c) may include: a process c1) of putting a cover on the metal layer; a process c2) of filling the processing hole with a transparent material; and a process c3) of removing the cover when the transparent material is hardened to form a board, and the cover enables the board and a surface of the metal layer to line up with each other.

In an exemplary embodiment of the present invention, the transparent material may be a polymer containing polydimethylsiloxane (PDMS) or parylene.

In an exemplary embodiment of the present invention, the process d) may include: a process d1) of cutting the wafer to form an electrode pillar; and a process d2) of performing chemical etching to the electrode pillar to form the electrode.

In an exemplary embodiment of the present invention, in the process d1), the wafer may be cut through deep reactive ion etching or dicing to form the electrode pillar.

In an exemplary embodiment of the present invention, in the process d2), the electrode pillar may be cut through isotropic wet etching to form the electrode.

In an exemplary embodiment of the present invention, in the process e), the deposition layer may be formed by depositing a metal thin film containing platinum (Pt) or iridium oxide (IrOx) on an end portion of the electrode, and the deposition layer may be provided to reduce the impedance of the electrode.

In an exemplary embodiment of the present invention, the process f) may include: a process f1) of combining the board and the electrode with an upper part of the circuit and preparing an insulation support unit; a process f2) of inserting the deposition layer into the insulation support unit; a process f3) of forming an insulating layer on external surfaces of the insulation support unit, the board, the electrode and the circuit; and a process f4) of removing the insulation support unit.

In an exemplary embodiment of the present invention, in the process f1), the insulation support unit may include a photosensitive layer formed of photoresist, and in the process f2), the deposition layer may be inserted into the photosensitive layer.

In an exemplary embodiment of the present invention, the process f) may include: a process f1) of preparing an insulation support unit; a process f2) of inserting the deposition layer into the insulation support unit; a process f3) of combining the board and the electrode with an upper part of an auxiliary pad and forming an insulating layer on external surfaces of the insulation support unit, the board, the electrode and the auxiliary pad; a process f4) of removing the insulation support unit and the auxiliary pad and combining a circuit with lower parts of the board and the electrode; and a process f5) of forming an insulating layer on an external surface of the circuit.

In an exemplary embodiment of the present invention, the process f5) may include: a process f51) of inserting the electrode into the insulation support unit to attach a lower surface of the insulation support unit to an upper surface of the board; a process f52) of forming an insulating layer on external surfaces of the insulation support unit, the board, and the circuit; and a process f53) of removing the insulation support unit.

In an exemplary embodiment of the present invention, the process f) may include: a process f1) of combining the board and the electrode with an upper part of an auxiliary pad; a process f2) of forming an insulating layer on external surfaces of the board, the electrode and the auxiliary pad; a process f3) of removing an insulating layer formed on an external surface of the deposition layer to expose the deposition layer; a process f4) of removing the auxiliary pad and combining the board and the electrode with an upper part of a circuit; and a process f5) of forming an insulating layer on an external surface of the circuit.

In an exemplary embodiment of the present invention, the process f5) may include: a process f51) of inserting the electrode into an insulation support unit to attach a lower surface of the insulation support unit to an upper surface of the board; a process f52) of forming an insulating layer on external surfaces of the insulation support unit, the board, and the circuit; and a process f53) of removing the insulation support unit.

DETAILED DESCRIPTION OF THE PREFERRED EMBODIMENTS

Figure 1:
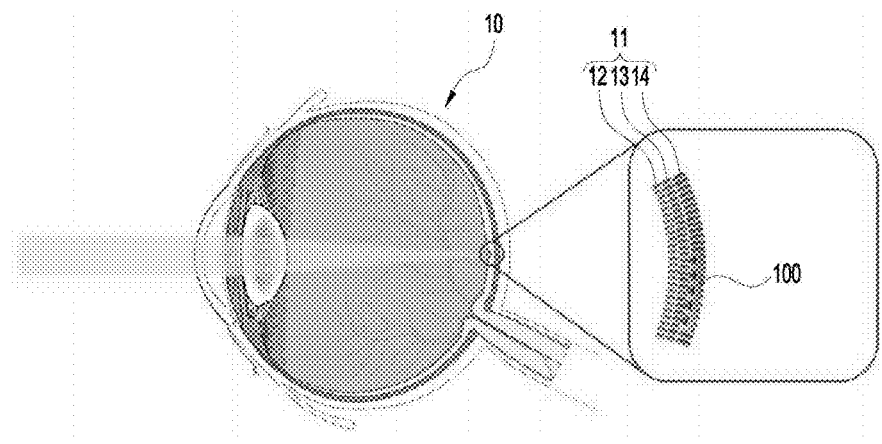
FIG. 1 is an illustration of an example of an insertion position of a three-dimensional electrode device in the retina according to an embodiment of the present invention.

Hereafter, the present invention will be described with reference to the accompanying drawings. However, it is to be noted that the present invention is not limited to the exemplary embodiments but can be embodied in various other ways. In the drawings, parts irrelevant to the description are omitted for the simplicity of explanation, and like reference numerals denote like parts through the whole document.

Throughout this document, the term "connected to (linked to, attached to, or combined with)" may be used to designate a connection or coupling of one element to another element and includes both an element being "directly connected to" another element and an element being "indirectly connected to" another element via another element. Further, the term "comprises or includes" and/or "comprising or including" used in the document means that one or more other components, steps, operation and/or existence or addition of elements are not excluded in addition to the described components, steps, operation and/or elements unless context dictates otherwise.

The terms used herein are used only to describe specific examples, but do not intend to limit the present invention. A singular expression includes a plural expression unless it is clearly construed in a different way in the context. The terms used herein, such as "including" or "having", are used only to designate the features, numbers, steps, operations, constituent elements, parts, or combinations thereof described in the specification, but should be construed not to exclude existence or addition of one or more other features, numbers, steps, operations, constituent elements, parts, or combinations thereof.

Hereafter, exemplary embodiments of the present invention will be described in detail with reference to the accompanying drawings.

FIG. 1 is an illustration of an example of an insertion position of a three-dimensional electrode device in the retina according to an embodiment of the present invention.

Referring to FIG. 1, an eyeball 10 has a retina 11 including a ganglion cell layer 12, a bipolar cell layer 13, and a photoreceptor layer 14, and a three-dimensional electrode device 100 may be placed in the photoreceptor layer 14.

The three-dimensional electrode device 100 may be prepared to be inserted into the photoreceptor layer 14. More specifically, the three-dimensional electrode device 100 may be inserted between the bipolar cell layer 13 and the photoreceptor layer 14. The three-dimensional electrode device 100 can also be prepared to be inserted into the suprachoroid or attached to the surface of the ganglion cell layer 12.

Figure 2:
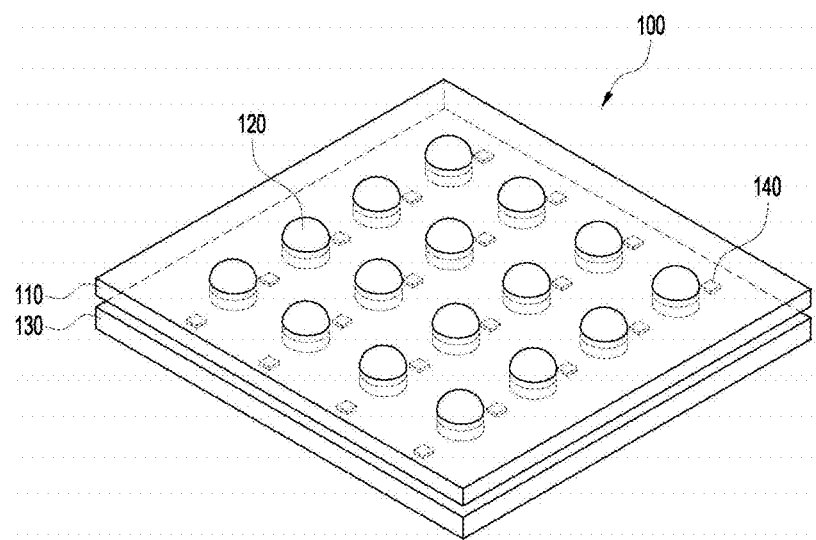
FIG. 2 is a perspective view of a retinal stimulator including the three-dimensional electrode device according to an embodiment of the present invention.
Figure 3:
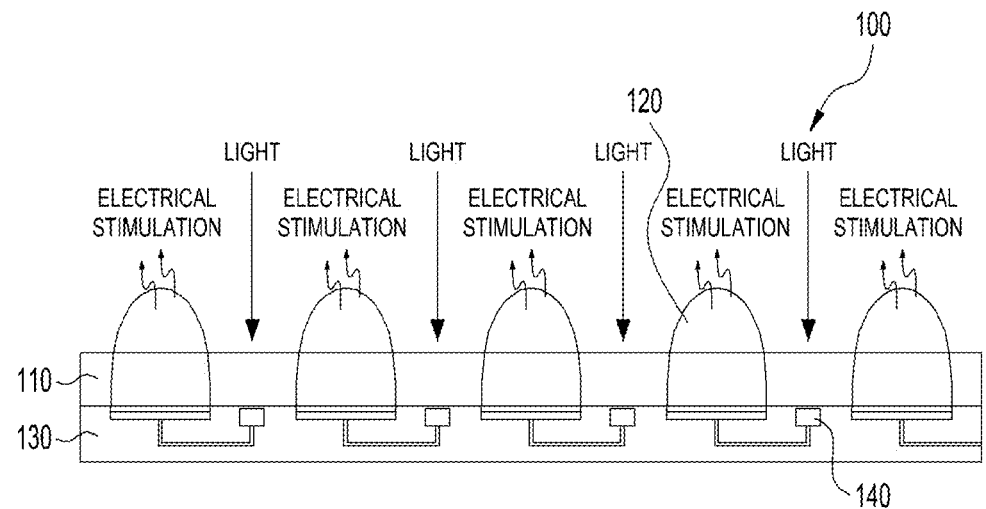
FIG. 3 illustrates an example operation of the retinal stimulator including the three-dimensional electrode device according to an embodiment of the present invention.

FIG. 2 is a perspective view of a retinal stimulator including the three-dimensional electrode device according to an embodiment of the present invention, and FIG. 3 illustrates an example operation of the retinal stimulator including the three-dimensional electrode device according to an embodiment of the present invention.

Referring to FIG. 2 and FIG. 3, the three-dimensional electrode device 100 includes a board 110 and multiple of electrodes 120 and can be combined with a circuit 130 including a photo diode 140. The board 110 and the electrodes 120 may be prepared to be deformed corresponding to a shape of the retina 11 and configured to make the electrodes 120 be in close contact with the retina 11.

The board 110 is prepared to be inserted into the photoreceptor layer 14 in the eyeball 10 and may be formed of a transparent material.

Further, the board 110 may be formed of a flexible material so as to be deformed corresponding to a shape of the retina 11.

Furthermore, the board 110 may be formed of a transparent material such as a polymer including polydimethylsiloxane (PDMS) or parylene in order for light incident into the eyeball 10 to pass through the eyeball and reach the photo diode 140.

To be specific, conventionally, an image signal has been transmitted to an electrode from an external device such as a camera, and the electrode has transferred the received image signal to a user through electrical stimulation. Thus, there has been no need to form the board 110 of a transparent material. However, in the present invention, image information taken by a camera or the like is not transmitted to an electrode, but light incident through an eye of a user is converted into an electrical signal by a photo diode 140. Thus, the board 110 needs to be formed of a transparent material.

The electrode 120 is formed on the board 110 and a plurality of electrodes may be prepared to stimulate the ganglion cell layer 12 and bipolar cell layer 13.

Figure 4:
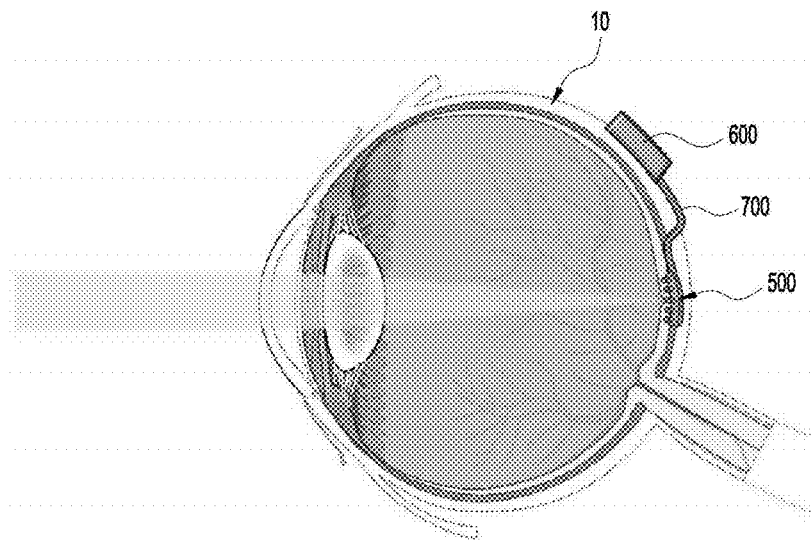
FIG. 4 is an illustration of an example of an insertion position of a three-dimensional electrode device according to another embodiment of the present invention.
Figure 5:
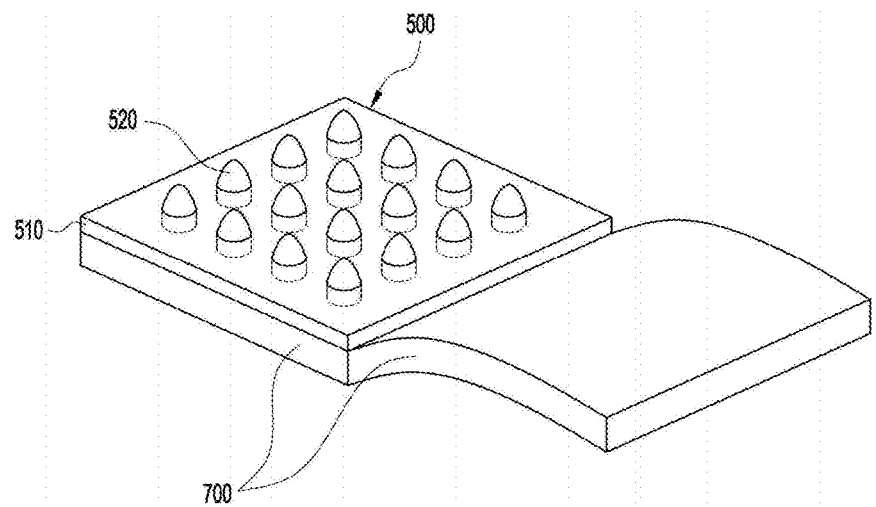
FIG. 5 is a perspective view of the three-dimensional electrode device according to another embodiment of the present invention.

FIG. 4 is an illustration of an example of an insertion position of a three-dimensional electrode device according to another embodiment of the present invention, and FIG. 5 is a perspective view of the three-dimensional electrode device according to another embodiment of the present invention.

As illustrated in FIG. 4 and FIG. 5, a three-dimensional electrode device 500 according to another embodiment may be prepared to be inserted into the photoreceptor layer 14. More specifically, the three-dimensional electrode device 500 may be inserted between the bipolar cell layer 13 and the photoreceptor layer 14. The three-dimensional electrode device 500 can also be prepared to be inserted into the suprachoroid or attached to the surface of the ganglion cell layer 12.

The three-dimensional electrode device 500 includes a board 510 and an electrode 520, the board 510 may be prepared to be deformed corresponding to a shape of the ganglion cell layer 12 and the bipolar cell layer 13 and configured to make the electrode 520 be in close contact with the ganglion cell layer 12 and the bipolar cell layer 13.

The board 510 is prepared to be inserted into the photoreceptor layer 14 in the eyeball 10 and may be formed of a transparent material.

Further, the board 510 may be formed of a flexible material so as to be deformed corresponding to a shape of the retina 11.

The electrode 520 is formed on the board 510 and a plurality of electrodes may be prepared to stimulate the ganglion cell layer 12 and bipolar cell layer 13.

Meanwhile, a stimulation unit 600 is prepared on the outside of the eyeball 10, and the stimulation unit 600 may be connected to the three-dimensional electrode device 500 through a routing circuit 700.

Specifically, the routing circuit 700 may be prepared in the form of a cable, and one end thereof may be connected to a lower surface of the board 110 of the three-dimensional electrode device 500 and the other end may be connected to the stimulation unit 600.

Further, the stimulation unit 600 may be equipped with a current generator that generates an electrical signal and an amplifier that amplifies the electrical signal.

Hereafter, an operation thereof will be described. Firstly, an external camera (not illustrated) may receive light information and convert the light information into a digital signal and then transmit the digital signal wirelessly to the stimulation unit 600. Herein, the external camera may be a small camera to be installed in glasses or the like.

The stimulation unit 600 may convert the received digital signal into an electrical signal to generate an electrical pulse.

Then, the electrical pulse generated by the stimulation unit 600 may be transferred to the electrode 520 of the three-dimensional electrode device 500 through the circuit 700. Then, the electrode 520 may apply electrical stimulation to the ganglion cell layer 12 and bipolar cell layer 13 with the received electrical pulse.

Figure 6:
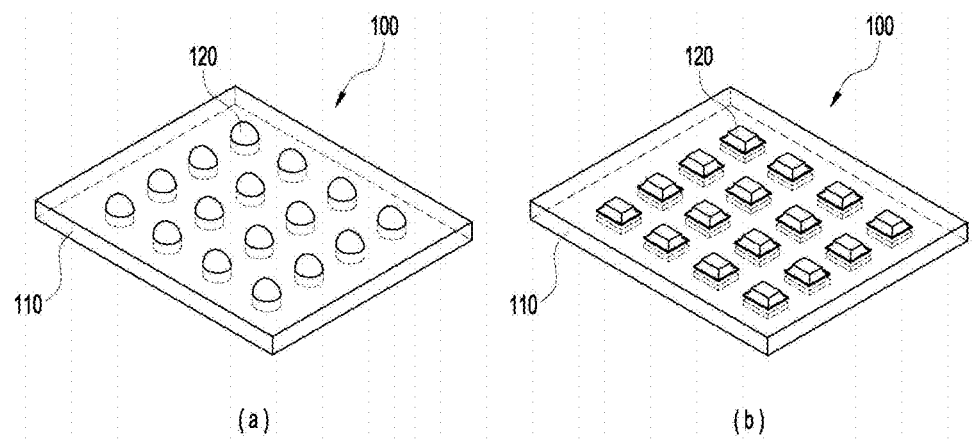
FIG. 6 is a perspective view illustrating an example shape of an electrode in the three-dimensional electrode device according to an embodiment of the present invention.

FIG. 6 is a perspective view illustrating an example shape of an electrode in the three-dimensional electrode device according to an embodiment of the present invention.

As illustrated in FIG. 6, the electrode 120 may be prepared to have a curved surface or flat surface to be attached to the retina 11 and thus may suppress damage to the retina 11 when the electrode 120 is in close contact with the target cells in the retina 11.

Figure 7:
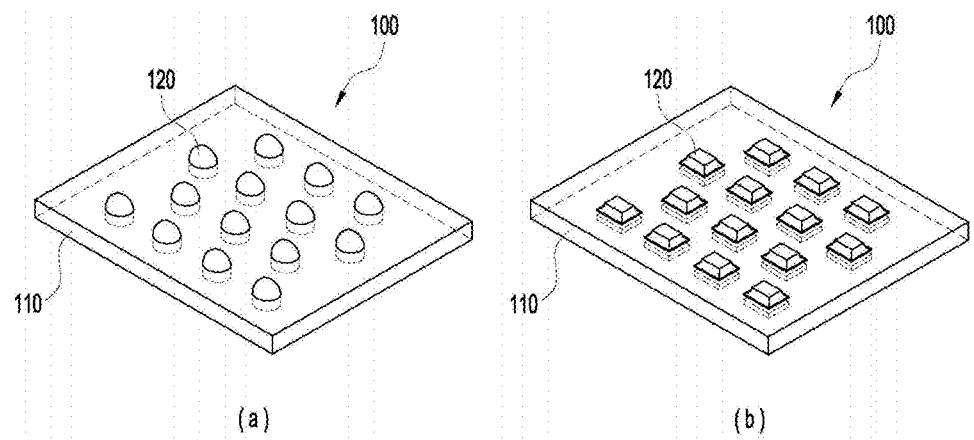
FIG. 7 is a perspective view illustrating an example layout of electrodes in the three-dimensional electrode device according to an embodiment of the present invention.

FIG. 7 is a perspective view illustrating an example layout of electrodes in the three-dimensional electrode device according to an embodiment of the present invention.

As illustrated in FIG. 7, the electrodes 120 may be arranged in a lattice shape or hexagonal shape or arranged with alternating rows or columns on the board 110.

Referring to FIG. 2 again, the circuit 130 may be combined with a lower part of the board 110.

The circuit 130 may suppress mutual electrical interference between the electrodes 120.

The photo diode 140 is prepared on an upper side of the circuit 130 and may be electrically connected to the electrode 120.

To be specific, the photo diode 140 is prepared on the upper side of the circuit 130 and located on one side of the electrode 120. The photo diode 140 prepared as such enables light passing through the transparent board 110 to be incident without being blocked by the electrode 120.

Further, the photo diode 140 may convert light energy incident through the board 110 into electric energy and provide the converted electric energy to the electrode 120 and thus enable the electrode 120 to stimulate the retina or measure an electrical signal from the retina.

Herein, the photo diode 140 may further include an optical sensor and a light source such as an optical fiber, and an LED.

Further, the application of the present invention is not limited to the retina and can be expanded to the brain, the spinal cord, the peripheral nerves, and the like.

Figure 8:
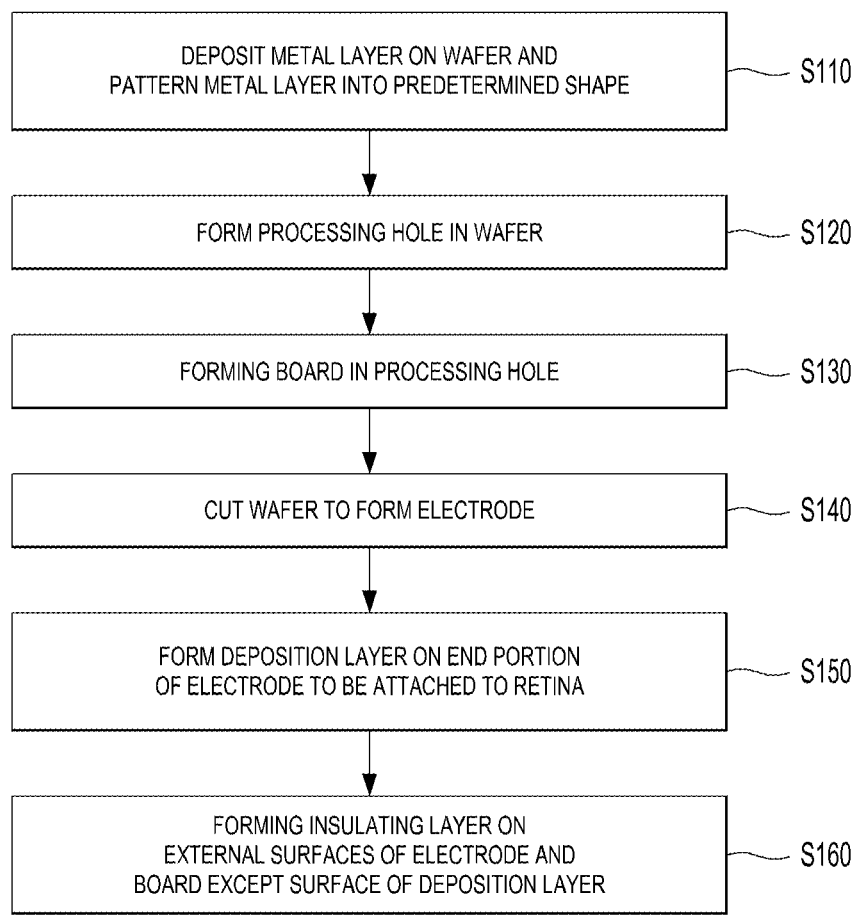
FIG. 8 is a flowchart illustrating a method for manufacturing a three-dimensional electrode device according to an embodiment of the present invention.
Figure 9:
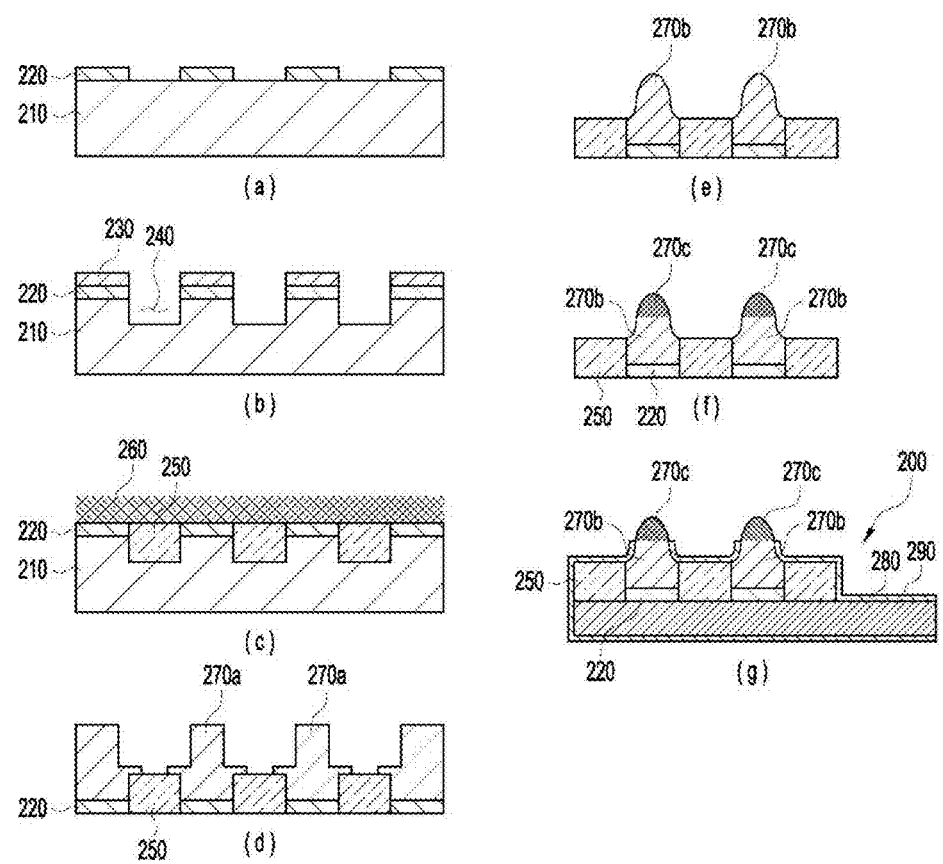
FIG. 9 illustrates an example processing flow for manufacturing a three-dimensional electrode device according to an embodiment of the present invention.

FIG. 8 is a flowchart illustrating a method for manufacturing a three-dimensional electrode device according to an embodiment of the present invention, and FIG. 9 illustrates an example processing flow for manufacturing the three-dimensional electrode device according to an embodiment of the present invention.

Hereafter, a method for manufacturing a three-dimensional electrode device will be described with reference to FIG. 8 and FIG. 9.

The method for manufacturing a three-dimensional electrode device includes a process of depositing a metal layer on a wafer and patterning the metal layer into a predetermined shape (S110), a process of forming a processing hole in the wafer (S120), a process of forming a board in the processing hole (S130), a process of cutting the wafer to form an electrode (S140), a process of forming a deposition layer on an end portion of the electrode to be attached to a retina (S150), and a process of forming an insulating layer on external surfaces of the electrode and the board except a surface of the deposition layer (S160). Hereafter, the processes will be described sequentially with reference to the accompanying drawings.

Figure 10:
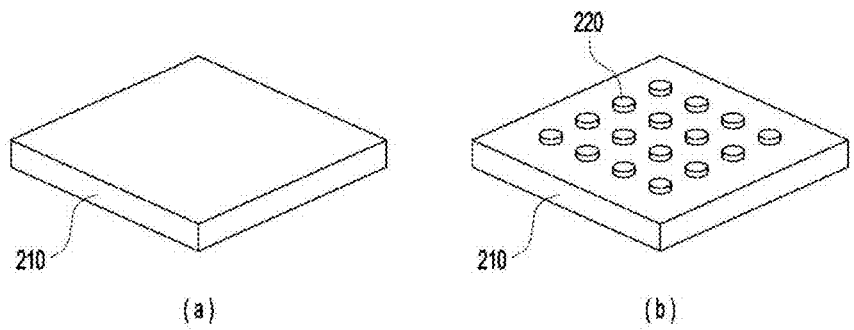
FIG. 10 is an illustration of an example of a patterning process in the method for manufacturing a three-dimensional electrode device according to an embodiment of the present invention.

FIG. 10 is an illustration of an example of a patterning process in the method for manufacturing a three-dimensional electrode device according to an embodiment of the present invention.

Referring to FIG. 10, in the method for manufacturing a three-dimensional electrode device, the process of depositing a metal layer on a wafer and patterning the metal layer into a predetermined shape (S110) may be performed.

In the process of depositing a metal layer on a wafer and patterning the metal layer into a predetermined shape (S110), the wafer 210 may be formed of silicon and the metal layer 220 may be formed of gold (Au) and titanium (Ti) or gold and chromium (Cr).

Herein, the titanium or the chromium may be contained to enhance an attachment between the gold and the wafer 210.

The metal layer 220 prepared as such is deposited on the wafer 210 and may be patterned into a predetermined shape. More specifically, the metal layer 220 may be deposited except where a board 250 is to be formed.

Figure 11:
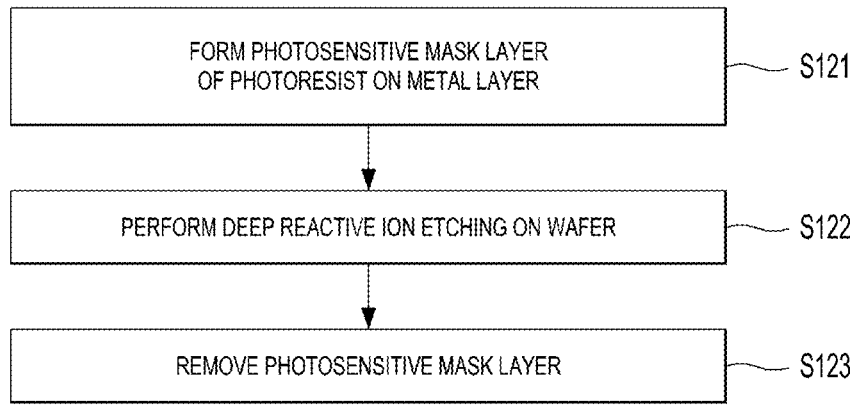
FIG. 11 is a flowchart illustrating a process for forming a processing hole in the method for manufacturing a three-dimensional electrode device according to an embodiment of the present invention.
Figure 12:
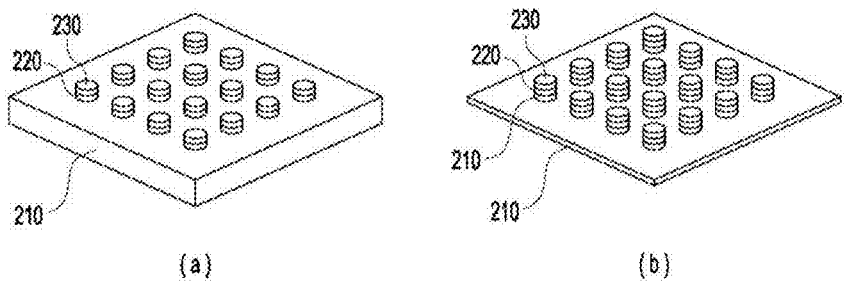
FIG. 12 is an illustration of an example of the process for forming a processing hole in the method for manufacturing a three-dimensional electrode device according to an embodiment of the present invention.

FIG. 11 is a flowchart illustrating a process for forming a processing hole in the method for manufacturing a three-dimensional electrode device according to an embodiment of the present invention, and FIG. 12 is an illustration of an example of the process for forming a processing hole in the method for manufacturing a three-dimensional electrode device according to an embodiment of the present invention.

Referring to FIG. 11 and FIG. 12, after the process of depositing a metal layer on a wafer and patterning the metal layer into a predetermined shape (S110), the process of forming a processing hole in the wafer (S120) may be performed.

In the process of forming a processing hole in the wafer (S120), a process of forming a photosensitive mask layer of photoresist on the metal layer (S121) may be performed first.

In the process of forming a photosensitive mask layer of photoresist on the metal layer (S121), the photosensitive mask layer 230 may be formed of photoresist and coated on the metal layer 220.

After the process of forming a photosensitive mask layer of photoresist on the metal layer (S121), a process of performing deep reactive ion etching to the wafer (S122) may be performed.

In the process of performing deep reactive ion etching to the wafer (S122), deep reactive ion etching may be performed to the wafer 210. In this case, the deep reactive ion etching may be performed to form a processing hole 240 only in a part except a part covered with the photosensitive mask layer 230.

After the process of performing deep reactive ion etching to the wafer (S122), a process of removing the photosensitive mask layer (S123) may be performed.

Figure 13:
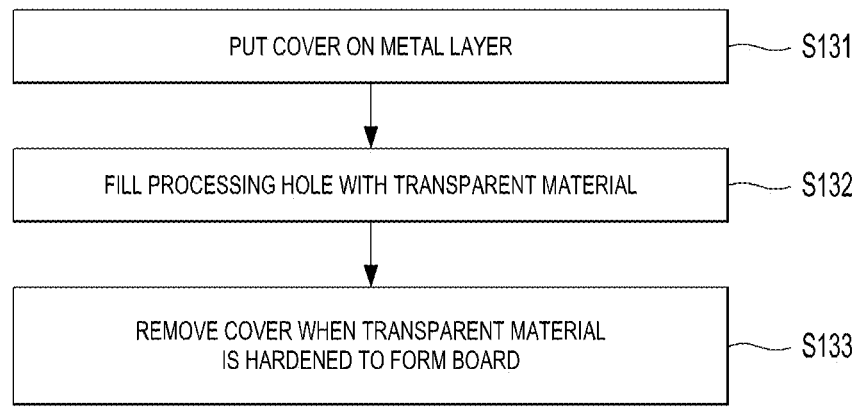
FIG. 13 is a flowchart illustrating a process for forming a board in the processing hole in the method for manufacturing a three-dimensional electrode device according to an embodiment of the present invention.
Figure 14:
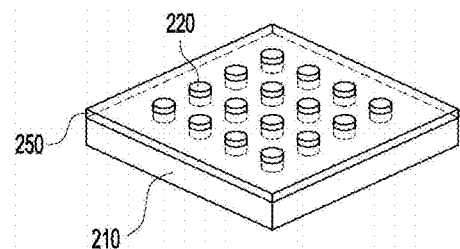
FIG. 14 is a perspective view of an electrode device during the process for forming the board in the processing hole in the three-dimensional electrode device according to an embodiment of the present invention.

FIG. 13 is a flowchart illustrating a process for forming a board in the processing hole in the method for manufacturing a three-dimensional electrode device according to an embodiment of the present invention, and FIG. 14 is a perspective view of an electrode device during the process for forming the board in the processing hole in the three-dimensional electrode device according to an embodiment of the present invention.

Referring to FIG. 13 and FIG. 14, after the process of forming a processing hole in the wafer (S120), the process of forming a board in the processing hole (S130) may be performed.

In the process of forming a board in the processing hole (S130), a process of putting a cover on the metal layer (S131) may be performed first.

More specifically, the cover 260 may be provided to cover an upper part of the metal layer 220. The cover 260 provided to cover the upper part of the metal layer 220 enables the board 250 and a surface of the metal layer 220 to line up with each other.

After the process of putting a cover on the metal layer (S131), a process of filling the processing hole with a transparent material (S132) may be performed.

Specifically, the processing hole 240 may be filled with a transparent material which is clear and flexible.

Herein, the transparent material may be a polymer including polydimethylsiloxane (PDMS) or parylene, and the transparent material may be hardened to form the board 250.

In the process of filling the processing hole with a transparent material (S132), the transparent material filled in the processing hole has the same level due to the cover 260. That is, when the transparent material is hardened to form the board 250, the board 250 may be formed to have the same thickness.

After the process of filling the processing hole with a transparent material (S132), a process of removing the cover (S133) may be performed when the transparent material is hardened to form the board.

Figure 15:
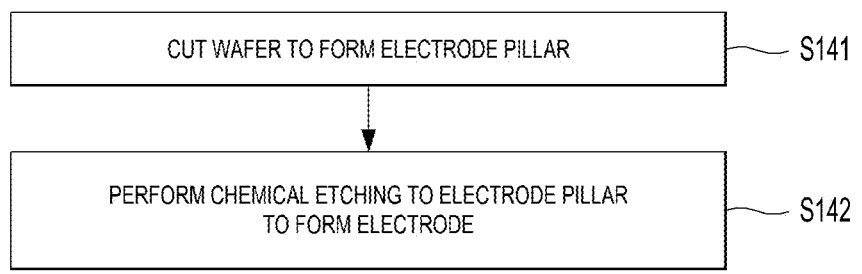
FIG. 15 is a flowchart illustrating a process for forming electrodes in the method for manufacturing a three-dimensional electrode device according to an embodiment of the present invention.
Figure 16:
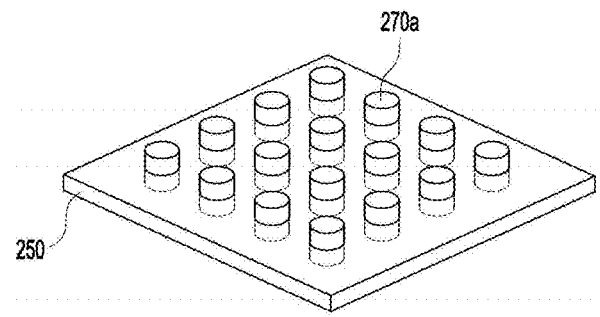
FIG. 16 is a perspective view of the electrode device during a process for forming an electrode pillar in the three-dimensional electrode device according to an embodiment of the present invention.
Figure 17:
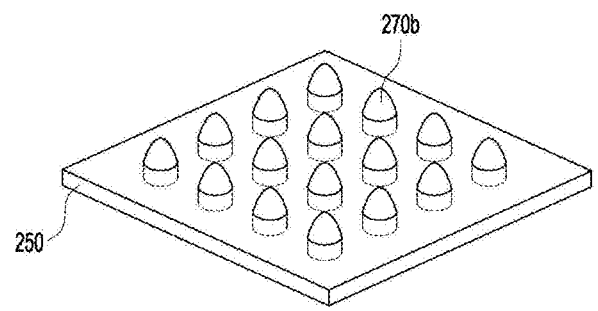
FIG. 17 is a perspective view of the electrode device during the process for forming electrodes in the three-dimensional electrode device according to an embodiment of the present invention.

FIG. 15 is a flowchart illustrating a process for forming electrodes in the method for manufacturing a three-dimensional electrode device according to an embodiment of the present invention, FIG. 16 is a perspective view of the electrode device during a process for forming an electrode pillar in the three-dimensional electrode device according to an embodiment of the present invention, and FIG. 17 is a perspective view of the electrode device during the process for forming electrodes in the three-dimensional electrode device according to an embodiment of the present invention.

Referring to FIG. 15 through FIG. 17, after the process of forming a board in the processing hole (S130), the process of cutting the wafer to form electrodes (S140) may be performed.

In the process of cutting the wafer to form electrodes (S140), a process of cutting the wafer to form electrode pillars (S141) may be performed first.

In the process of cutting the wafer to form electrode pillars (S141), an upper part of the wafer 210 may be rotated downwards and then deep reactive ion etching or dicing may be performed to the wafer 210. Through this process, the wafer 210 may be cut to form the electrode pillar 270a.

After the process of cutting the wafer to form electrode pillars (S141), a process of performing chemical etching to the electrode pillar to form the electrode (S142) may be performed.

In the process of performing chemical etching to the electrode pillar to form the electrode (S142), the electrode pillar 270a may be cut through isotropic wet etching to form the electrode 270b.

In this case, an end portion of the electrode 270b may be formed to have a curved surface or flat surface.

Figure 18:
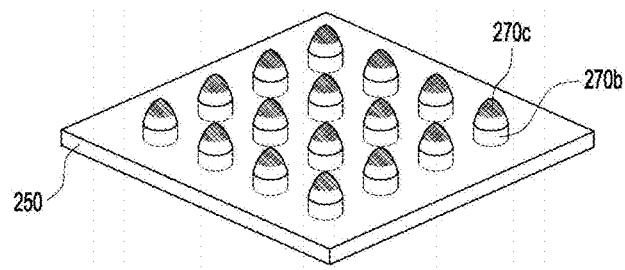
FIG. 18 is a perspective view of the electrode device during a process for forming a deposition layer in the three-dimensional electrode device according to an embodiment of the present invention.

FIG. 18 is a perspective view of the electrode device during a process for forming a deposition layer in the three-dimensional electrode device according to an embodiment of the present invention.

Referring to FIG. 18, after the process of cutting the wafer to form an electrode (S140), a process of forming a deposition layer on an end portion of the electrode to be attached to a retina (S150) may be performed.

In the process of forming a deposition layer on an end portion of the electrode to be attached to a retina (S150), the deposition layer 270c may be formed by depositing a metal thin film including platinum (Pt) or iridium oxide (IrOx) on an end portion of the electrode 270b and the deposition layer 270c can reduce the impedance of the electrode 270b.

Figure 19:
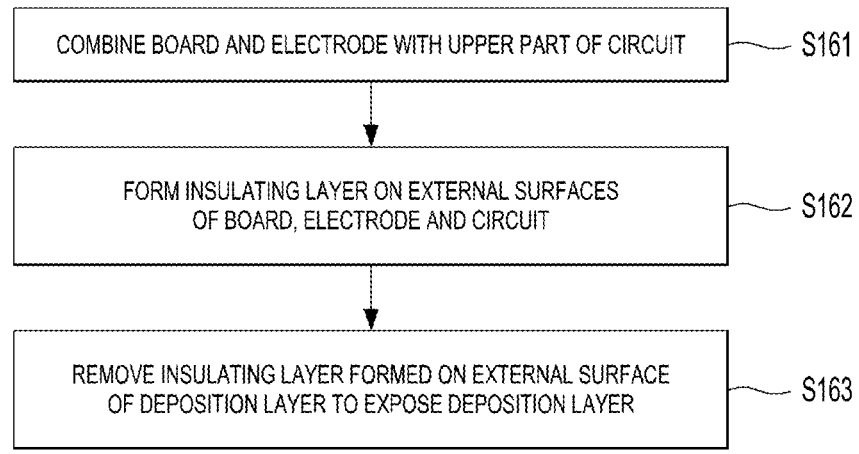
FIG. 19 is a flowchart illustrating a process for forming an insulating layer in a method for manufacturing a three-dimensional electrode device according to a first embodiment of the present invention.
Figure 20:
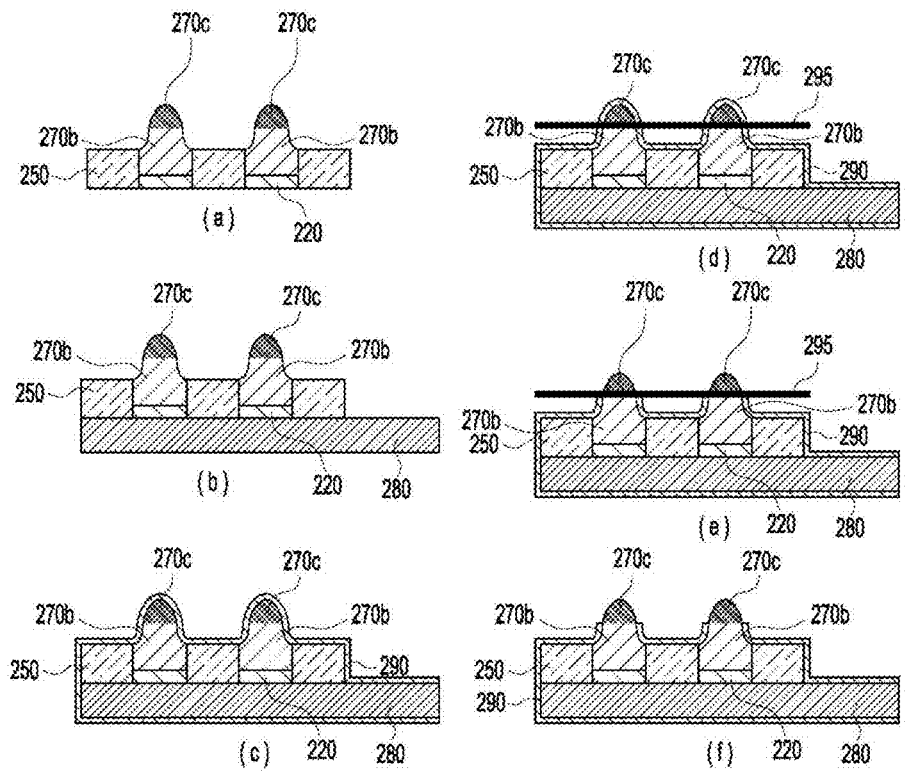
FIG. 20 illustrates an example processing flow for forming the insulating layer in the method for manufacturing a three-dimensional electrode device according to the first embodiment of the present invention.
Figure 21:
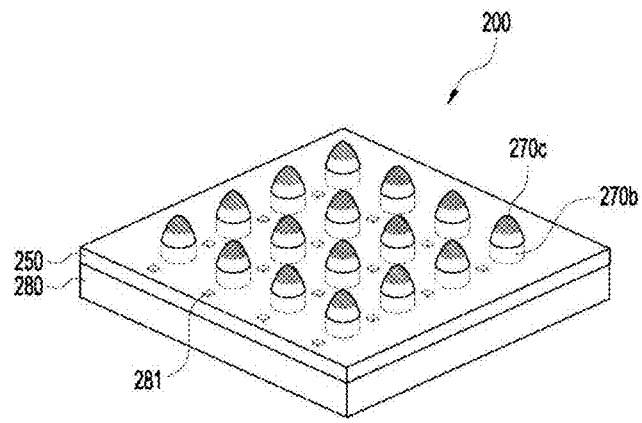
FIG. 21 is a perspective view of a three-dimensional electrode device manufactured by the method for manufacturing a three-dimensional electrode device according to the first embodiment of the present invention.

FIG. 19 is a flowchart illustrating a process for forming an insulating layer in a method for manufacturing a three-dimensional electrode device according to a first embodiment of the present invention, FIG. 20 illustrates an example processing flow for forming the insulating layer in the method for manufacturing a three-dimensional electrode device according to the first embodiment of the present invention, and FIG. 21 is a perspective view of a three-dimensional electrode device manufactured by the method for manufacturing a three-dimensional electrode device according to the first embodiment of the present invention. Referring to FIG. 19 through FIG. 12, after the process of forming a deposition layer on an end portion of the electrode to be attached to a retina (S150), a process of forming an insulating layer on external surfaces of the electrode and the board except a surface of the deposition layer (S160) may be performed.

In the process of forming an insulating layer on external surfaces of the electrode and the board except a surface of the deposition layer (S160) according to the first embodiment, a process of combining the board and the electrode with an upper part of the circuit (S161) may be performed first as illustrated in FIG. 20A and FIG. 20B.

In the process of combining the board and the electrode with an upper part of the circuit (S161), the electrode 270b can be combined together as the circuit 280 is combined with a lower part of the board 250.

Further, the electrode 270b combined with the circuit 280 may be electrically connected with the photo diode 140 (see FIG. 2) formed on the circuit 280.

After the process of combining the board and the electrode with an upper part of the circuit (S161), a process of forming an insulating layer on external surfaces of the board, the electrode and the circuit (S162) may be performed as illustrated in FIG. 20C.

In the process of forming an insulating layer on external surfaces of the board, the electrode and the circuit (S162), the insulating layer 290 may be formed by coating external surfaces of the board 250, the electrode 270b and the circuit 280 with a polymer material containing parylene.

After the process of forming an insulating layer on external surfaces of the board, the electrode and the circuit (S162), a process of removing an insulating layer formed on an external surface of the deposition layer to expose the deposition layer (S163) may be performed as illustrated in FIG. 20D through FIG. 20F.

In the process of removing an insulating layer formed on an external surface of the deposition layer to expose the deposition layer (S163), an auxiliary mask 295 may be formed first at a position corresponding to the depth of the deposition layer 270c to be exposed as illustrated in FIG. 20D. Then, as illustrated in FIG. 20E, the insulating layer 290 coated on an upper side of the auxiliary mask 295 is removed, and, thus, the insulating layer 290 formed on the end portion of the electrode 270b and coated on an external surface of the deposition layer 270c can be removed. After the insulating layer 290 is removed, the auxiliary mask 295 is removed.

As such, the deposition layer 270c with the insulating layer 290 removed from its external surface may be directly attached to the ganglion cell layer 12 and bipolar cell layer 13 of the retina 11 (see FIG. 1) to apply electrical stimulation to the retina 11 or measure an electrical signal from the retina 11.

Figure 22:
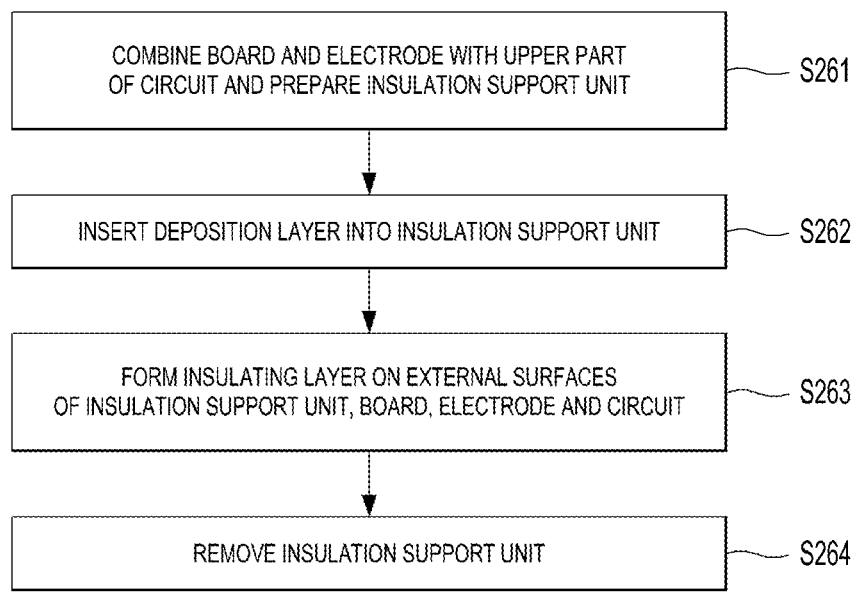
FIG. 22 is a flowchart illustrating a process for forming an insulating layer in a method for manufacturing a three-dimensional electrode device according to a second embodiment of the present invention.
Figure 23:
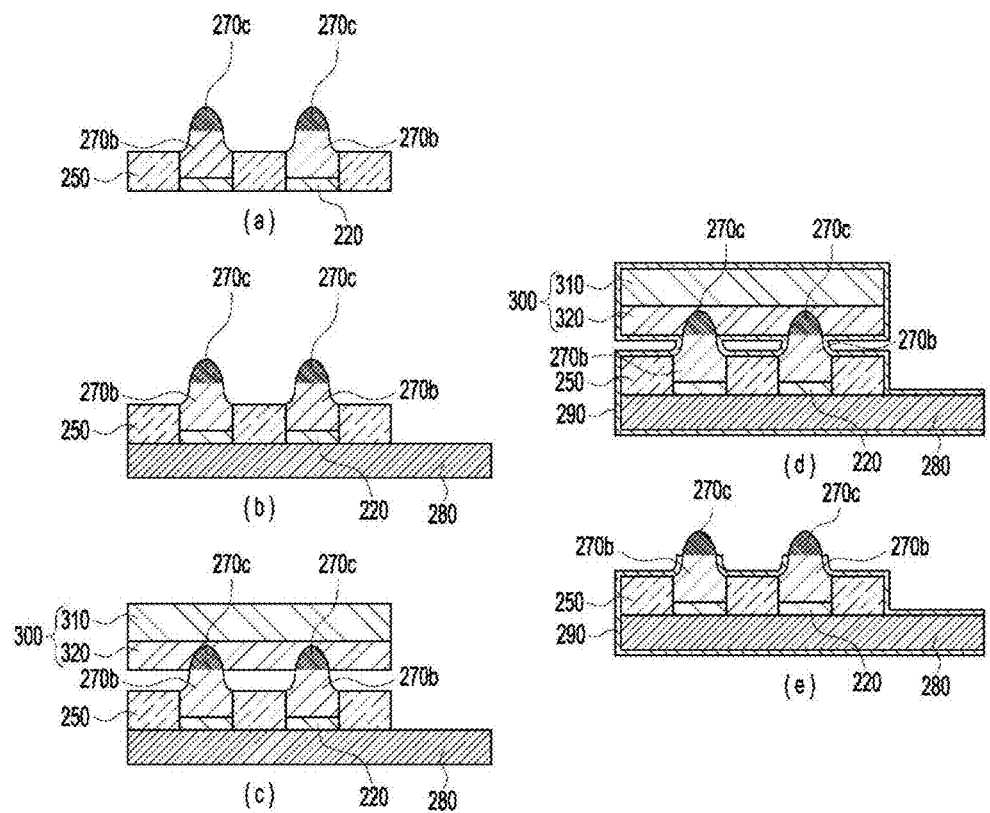
FIG. 23 illustrates an example processing flow for forming the insulating layer in the method for manufacturing a three-dimensional electrode device according to the second embodiment of the present invention.

FIG. 22 is a flowchart illustrating a process for forming an insulating layer in a method for manufacturing a three-dimensional electrode device according to a second embodiment of the present invention, and FIG. 23 illustrates an example processing flow for forming the insulating layer in the method for manufacturing a three-dimensional electrode device according to the second embodiment of the present invention. In the process of forming an insulating layer on external surfaces of the electrode and the board except a surface of the deposition layer (S160) according to the second embodiment, a process of combining the board and the electrode with an upper part of the circuit and preparing an insulation support unit (S261) may be performed first as illustrated in FIG. 23A through FIG. 23C.

In the process of combining the board and the electrode with an upper part of the circuit and preparing an insulation support unit (S261), the insulation support unit 300 includes a substrate 310 and a photosensitive layer 320.

The photosensitive layer 320 may be formed of photoresist. For example, the photosensitive layer 320 may be prepared by coating photoresist uniformly on one side of the substrate 310. Otherwise, the photosensitive layer 320 may be prepared by patterning photoresist into a shape corresponding to the electrode 270b on one side of the substrate 310.

After the process of combining the board and the electrode with an upper part of the circuit and preparing an insulation support unit (S261), a process of inserting the deposition layer into the insulation support unit (S262) may be performed.

In the process of inserting the deposition layer into the insulation support unit (S262), the deposition layer 270c may be inserted into the photosensitive layer 320.

Herein, if the photosensitive layer 320 is in a liquid state, the electrode 270b may be inserted into the photosensitive layer 320 in a liquid state and then the photosensitive layer 320 may be hardened.

After the process of inserting the deposition layer into the insulation support unit (S262), a process of forming an insulating layer on external surfaces of the insulation support unit, the board, the electrode and the circuit (S263) may be performed as illustrated in FIG. 23D.

In the process of combining the board and the electrode with an upper part of the circuit and forming an insulating layer on external surfaces of the insulation support unit, the board, the electrode and the circuit (S263), the board 250 and the electrode 270b may be combined with an upper part of the circuit 280. Further, in this state, the insulating layer 290 may be formed on external surfaces of the insulation support unit 300, the board 250, the electrode 270b and the circuit 280.

In this case, the deposition layer 270c is inserted in the photosensitive layer 320 as illustrated in FIG. 23C and thus is not exposed to the outside. Therefore, the insulating layer 290 is not formed on the external surface of the deposition layer 270c.

If the insulation support unit 300 is used to suppress the formation of the insulating layer 290 on the external surface of the deposition layer 270c, it is possible to suppress the peeling of the deposition layer 270c or damage to the electrode 270b which may occur when removing the insulating layer 290 formed on the external surface of the deposition layer 270c.

After the process of combining the board and the electrode with an upper part of the circuit and forming an insulating layer on external surfaces of the insulation support unit, the board, the electrode and the circuit (S263), a process of removing the insulation support unit (S264) may be performed as illustrated in FIG. 23E.

Figure 24:
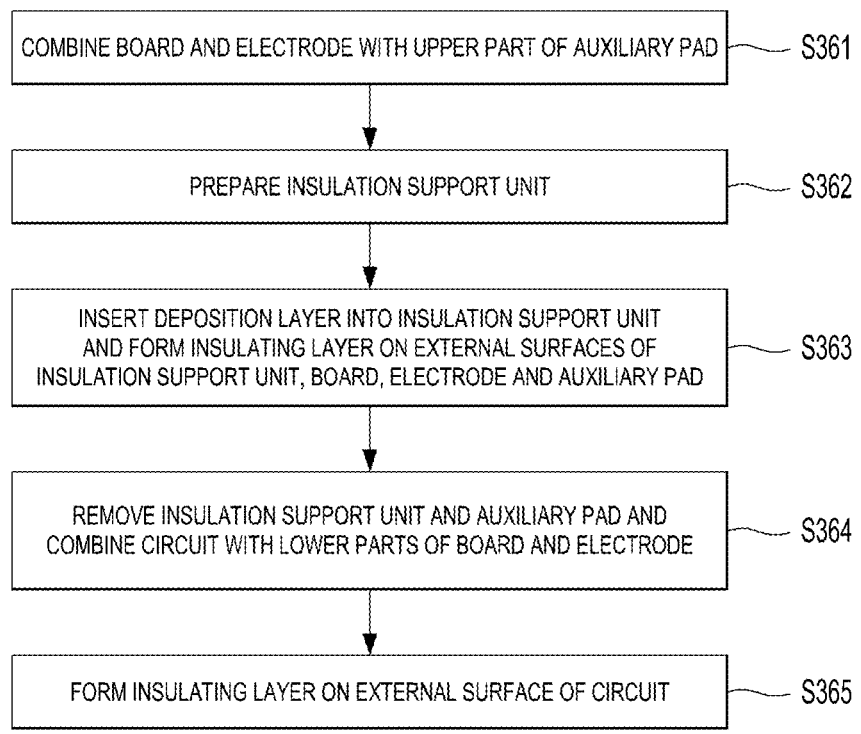
FIG. 24 is a flowchart illustrating a process for forming an insulating layer in a method for manufacturing a three-dimensional electrode device according to a third embodiment of the present invention.
Figure 25:
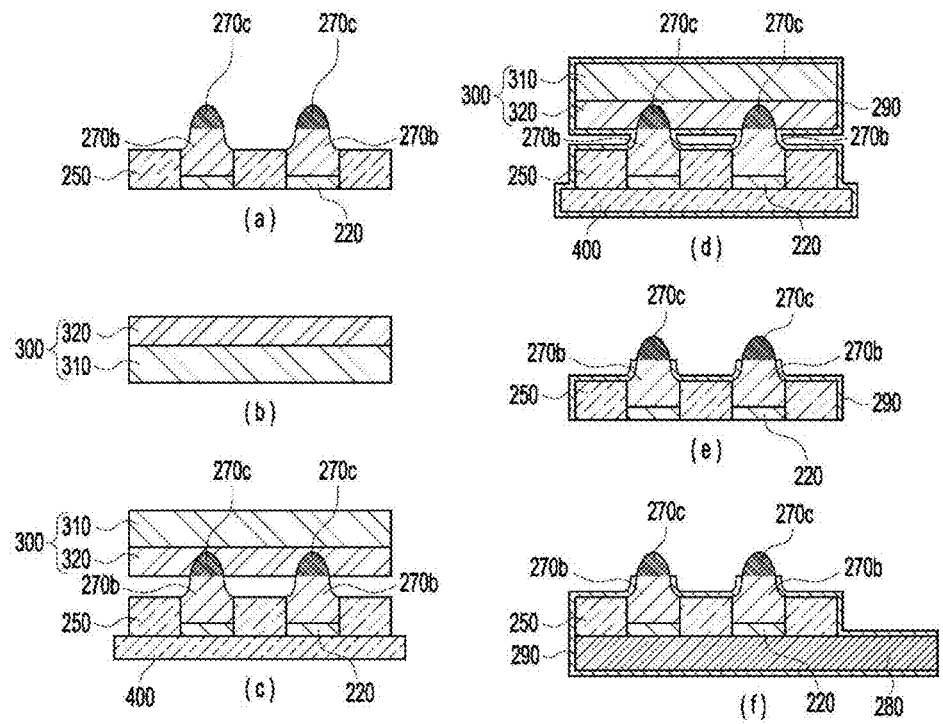
FIG. 25 illustrates an example processing flow for forming the insulating layer in the method for manufacturing a three-dimensional electrode device according to the third embodiment of the present invention.

FIG. 24 is a flowchart illustrating a process for forming an insulating layer in a method for manufacturing a three-dimensional electrode device according to a third embodiment of the present invention, and FIG. 25 illustrates an example processing flow for forming the insulating layer in the method for manufacturing a three-dimensional electrode device according to the third embodiment of the present invention.

As illustrated in FIG. 24 and FIG. 25, in the process of forming an insulating layer on external surfaces of the electrode and the board except a surface of the deposition layer (S160) according to the third embodiment of the present invention, a process of combining the board and the electrode with an upper part of an auxiliary pad (S361) may be performed.

In the process of combining the board and the electrode with an upper part of an auxiliary pad (S361), the board 250 and the electrode 270b may be combined with an upper part of the auxiliary pad 400.

After the process of combining the board and the electrode with an upper part of an auxiliary pad (S361), a process of preparing the insulation support unit (S362) may be performed. In the process of preparing the insulation support unit (S362), the insulation support unit 300 may include the substrate 310 and the photosensitive layer 320. The photosensitive layer 320 may be prepared by being coated in a liquid state uniformly on one side of the substrate 310 or by being patterned into a shape corresponding to the electrode 270b on one side of the substrate 310.

Herein, the photosensitive layer 320 may be formed of photoresist.

After the process of preparing the insulation support unit (S362), a process of inserting the deposition layer into the insulation support unit and forming an insulating layer on external surfaces of the insulation support unit, the board, the electrode and the auxiliary pad (S363) may be performed.

In the process of inserting the deposition layer into the insulation support unit and forming an insulating layer on external surfaces of the insulation support unit, the board, the electrode and the auxiliary pad (S363), the deposition layer 270c may be inserted into the photosensitive layer 320 in a liquid state. Then, while the deposition layer 270c is inserted into the photosensitive layer 320 in a liquid state, the photosensitive layer 320 may be hardened.

Further, in this state, the insulating layer 290 may be formed on the external surfaces of the insulation support unit 300, the board 250, the electrode 270b and the auxiliary pad 400.

In this case, the deposition layer 270c is inserted in the photosensitive layer 320 as illustrated in FIG. 25C and FIG. 25D and thus is not exposed to the outside. Therefore, the insulating layer 290 is not formed on the external surface of the deposition layer 270c.

If the insulation support unit 300 is used to suppress the formation of the insulating layer 290 on the external surface of the deposition layer 270c, it is possible to suppress the peeling of the deposition layer 270c or damage to the electrode 270b which may occur when removing the insulating layer 290 formed on the external surface of the deposition layer 270c.

Further, the auxiliary pad 400 is attached to lower parts of the board 250 and the electrode 270b, and, thus, the insulating layer 290 is not formed on lower surfaces of the board 250 and the electrode 270b.

After the process of inserting the deposition layer into the insulation support unit and forming an insulating layer on external surfaces of the insulation support unit, the board, the electrode and the auxiliary pad (S363), a process of removing the insulation support unit and the auxiliary pad and combining the circuit with lower parts of the board and the electrode (S364) may be performed as illustrated in FIG. 25E and FIG. 25F.

After the process of removing the insulation support unit and the auxiliary pad and combining the circuit with lower parts of the board and the electrode (S364), a process of forming an insulating layer on the external surface of the circuit (S365) may be performed.

Figure 26:
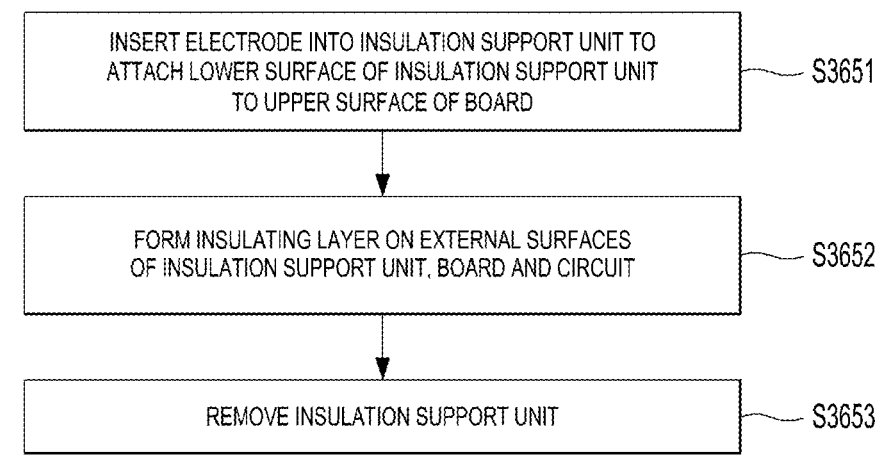
FIG. 26 is a flowchart illustrating a process for forming an insulating layer on an external surface of a circuit in the method for manufacturing a three-dimensional electrode device according to the third embodiment of the present invention.
Figure 27:
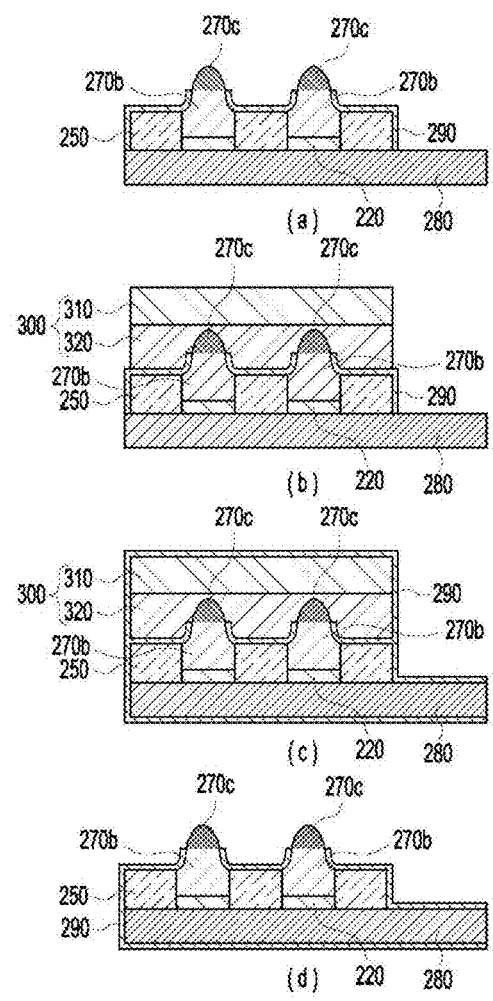
FIG. 27 illustrates an example processing flow for forming the insulating layer on the external surface of the circuit in the method for manufacturing a three-dimensional electrode device according to the third embodiment of the present invention.

FIG. 26 is a flowchart illustrating a process for forming an insulating layer on an external surface of a circuit in the method for manufacturing a three-dimensional electrode device according to the third embodiment of the present invention, and FIG. 27 illustrates an example processing flow for forming the insulating layer on the external surface of the circuit in the method for manufacturing a three-dimensional electrode device according to the third embodiment of the present invention.

Hereafter, the process of forming an insulating layer on the external surface of the circuit (S365) will be described in more detail with reference to FIG. 26 and FIG. 27.

In the process of forming an insulating layer on the external surface of the circuit (S365), a process of inserting the electrode into the insulation support unit to attach a lower surface of the insulation support unit to an upper surface of the board (S3651) may be performed first as illustrated in FIG. 27A and FIG. 27B.

That is, in the process of inserting the electrode into the insulation support unit to attach a lower surface of the insulation support unit to an upper surface of the board (S3651), the photosensitive layer 320 of the insulation support unit 300 may cover the electrode 270b and the deposition layer 270c to have no exposed part.

After the process of inserting the electrode into the insulation support unit to attach a lower surface of the insulation support unit to an upper surface of the board (S3651), a process of forming an insulating layer on the external surfaces of the insulation support unit, the board and the circuit (S3652) may be performed as illustrated in FIG. 27C.

In the process of forming an insulating layer on the external surfaces of the insulation support unit, the board and the circuit (S3652), the insulating layer 290 may be formed on the external surfaces of the insulation support unit 300 and the circuit 280 and the insulating layer 290 may also be formed secondarily on the insulating layer 290 previously formed on the external surface of the board 250.

After the process of secondarily forming an insulating layer on the external surfaces of the insulation support unit, the board and the circuit (S3652), a process of removing the insulation support unit (S3653) may be performed as illustrated in FIG. 27D.

Figure 28:
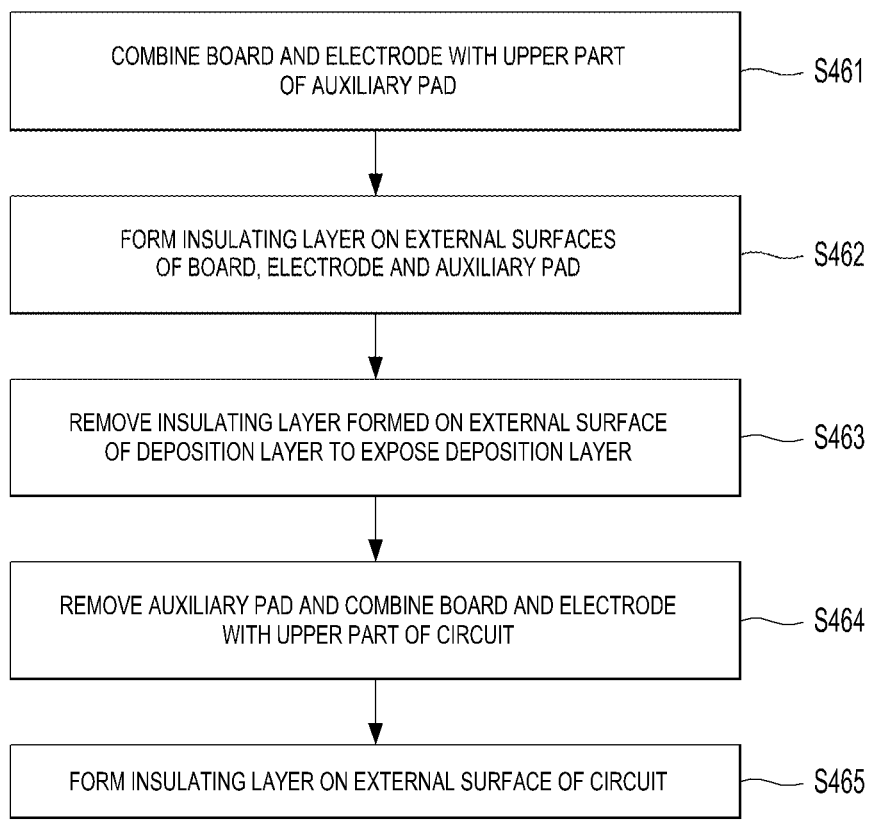
FIG. 28 is a flowchart illustrating a process for forming an insulating layer in a method for manufacturing a three-dimensional electrode device according to a fourth embodiment of the present invention.
Figure 29:
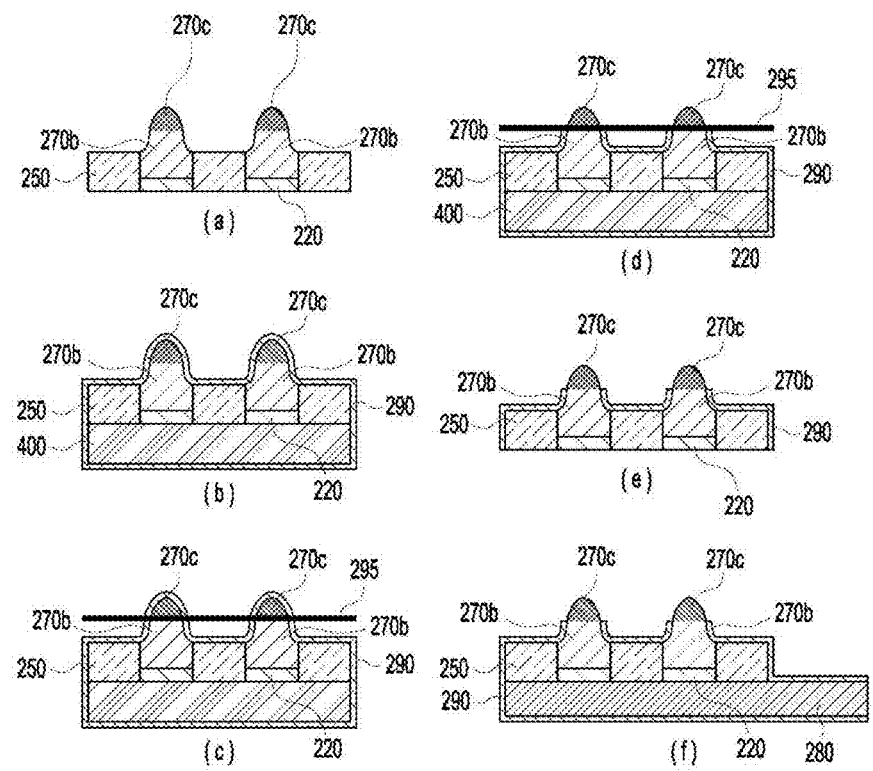
FIG. 29 illustrates an example processing flow for forming the insulating layer in the method for manufacturing a three-dimensional electrode device according to the fourth embodiment of the present invention.

FIG. 28 is a flowchart illustrating a process for forming an insulating layer in a method for manufacturing a three-dimensional electrode device according to a fourth embodiment of the present invention, and FIG. 29 illustrates an example processing flow for forming the insulating layer in the method for manufacturing a three-dimensional electrode device according to the fourth embodiment of the present invention.

In the process of forming an insulating layer on external surfaces of the electrode and the board except a surface of the deposition layer (S160) according to the fourth embodiment, a process of combining the board and the electrode with an upper part of an auxiliary pad (S461) may be performed first as illustrated in FIG. 28A and FIG. 28B.

In the process of combining the board and the electrode with an upper part of an auxiliary pad (S461), the electrode 270b can be combined together as the auxiliary pad is combined with the lower part of the board 250.

Further, the electrode 270b combined with the circuit 280 may be electrically connected with the photo diode 140 (see FIG. 2) formed on the circuit 280.

After the process of combining the board and the electrode with an upper part of an auxiliary pad (S161), a process of forming an insulating layer on external surfaces of the board, the electrode and the auxiliary pad (S462) may be performed as illustrated in FIG. 29B.

In the process of forming an insulating layer on external surfaces of the board, the electrode and the auxiliary pad (S162), the insulating layer 290 may be formed by coating external surfaces of the board 250, the electrode 270b and the auxiliary pad with a polymer material containing parylene.

After the process of forming an insulating layer on external surfaces of the board, the electrode and the auxiliary pad (S462), a process of removing an insulating layer formed on an external surface of the deposition layer to expose the deposition layer (S463) may be performed as illustrated in FIG. 29C and FIG. 29D.

In the process of removing an insulating layer formed on an external surface of the deposition layer to expose the deposition layer (S463), the auxiliary mask 295 may be formed first at a position corresponding to the depth of the deposition layer 270c to be exposed as illustrated in FIG. 29C. Then, as illustrated in FIG. 29D, the insulating layer 290 coated on an upper side of the auxiliary mask 295 is removed, and, thus, the insulating layer 290 formed on the end portion of the electrode 270b and coated on the external surface of the deposition layer 270c can be removed.

After the process of removing an insulating layer formed on an external surface of the deposition layer to expose the deposition layer (S463), a process of removing the auxiliary pad and combining the board and the electrode with an upper part of the circuit (S464) may be performed as illustrated in FIG. 29E and FIG. 29F.

After the process of removing the auxiliary pad and combining the board and the electrode with an upper part of the circuit (S464), a process of forming an insulating layer on the external surface of the circuit (S465) may be performed.

Figure 30:
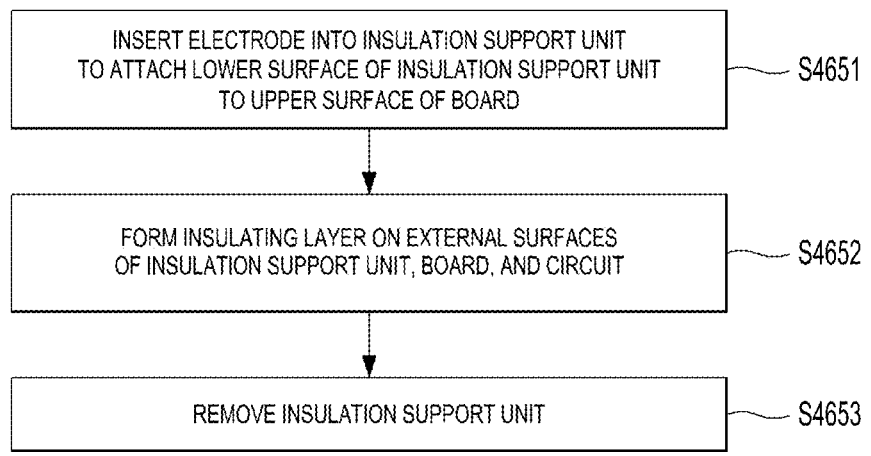
FIG. 30 is a flowchart illustrating a process for forming an insulating layer on an external surface of a circuit in the method for manufacturing a three-dimensional electrode device according to the fourth embodiment of the present invention.

FIG. 30 is a flowchart illustrating a process for forming an insulating layer on the external surface of a circuit in the method for manufacturing a three-dimensional electrode device according to the fourth embodiment of the present invention.

Referring to FIG. 30, in the process of forming an insulating layer on the external surface of the circuit (S465), a process of inserting the electrode into the insulation support unit to attach a lower surface of the insulation support unit to an upper surface of the board (S4651), a process of forming an insulating layer on external surfaces of the insulation support unit, the board, and the circuit (S4652) and a process of removing the insulation support unit (S4653) may be performed sequentially.

The process of forming an insulating layer on the external surface of the circuit (S465) according to the fourth embodiment is substantially the same as the process of forming an insulating layer on the external surface of the circuit (S365) according to the third embodiment. Therefore, a detailed explanation thereof will be omitted.

As described above, the process of forming an insulating layer on external surfaces of the electrode and the board except a surface of the deposition layer (S160) may be performed according to any one of the first to fourth embodiments.

Further, if the three-dimensional electrode device 100 according to an embodiment is manufactured, the photo diode 140 may be provided therein, and if the three-dimensional electrode device 500 according to another embodiment is manufactured, the photo diode 140 may not be provided therein.

Figure 31:
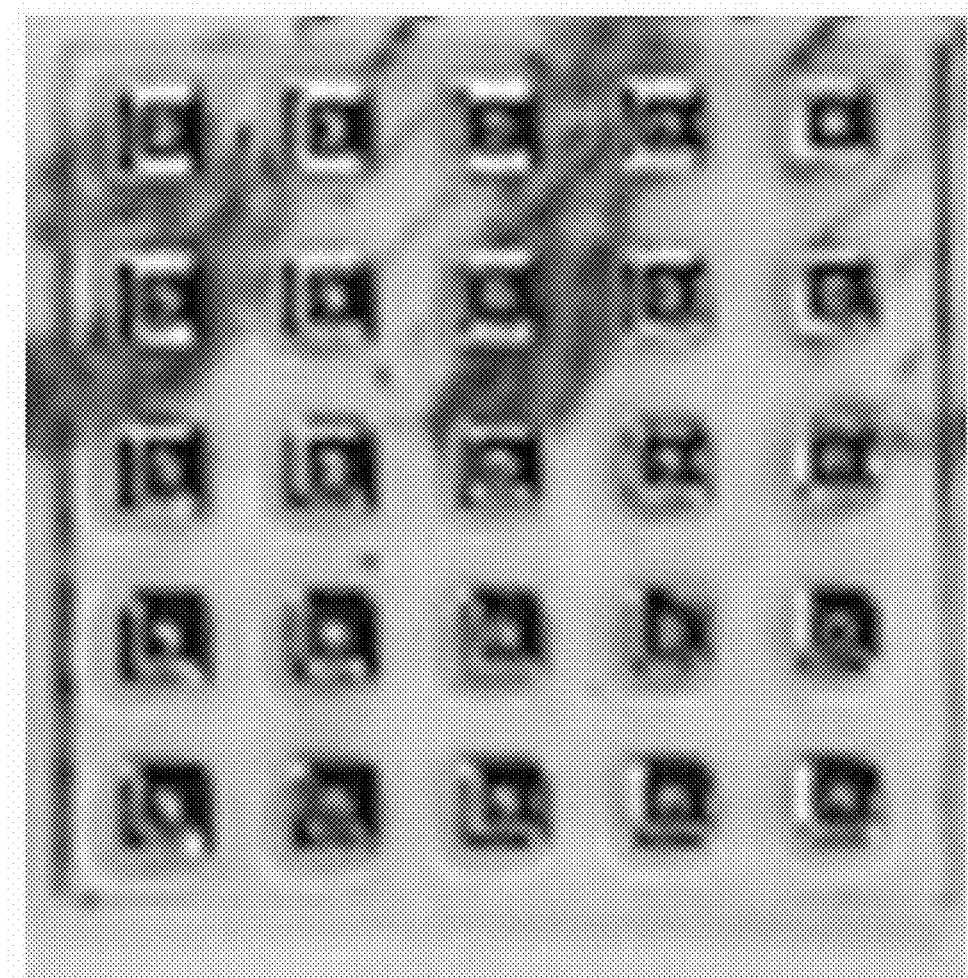
FIG. 31 is a photo showing an upper part of the three-dimensional electrode device according to an embodiment of the present invention.
Figure 32:
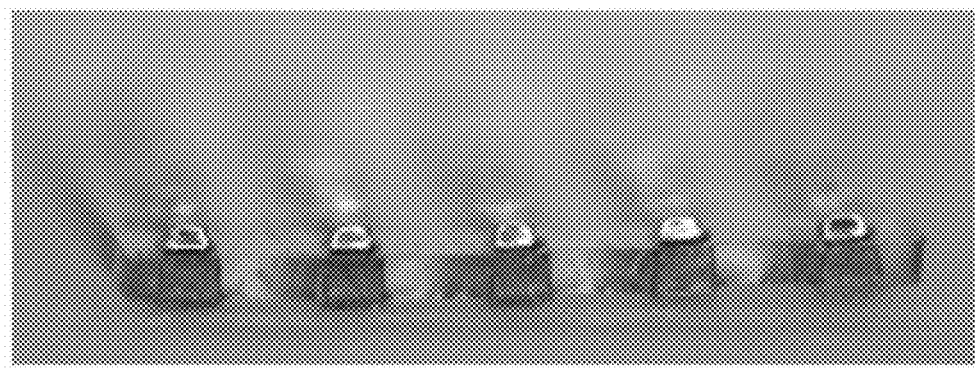
FIG. 32 is a photo showing a lateral surface of the three-dimensional electrode device according to an embodiment of the present invention.

FIG. 31 is a photo showing an upper part of the three-dimensional electrode device according to an embodiment of the present invention, and FIG. 32 is a photo showing a lateral surface of the three-dimensional electrode device according to an embodiment of the present invention.

As illustrated in FIG. 31 and FIG. 32, it can be seen that in a three-dimensional electrode device 200, the board 250 is formed of a transparent material and an end portion of the electrode 270b is not pointed but has a curved surface or flat surface.

The board 250 and the circuit 280 prepared as such according to the present invention are prepared to be deformed corresponding to a shape of the ganglion cell layer 12, the bipolar cell layer 13 and the photoreceptor layer 14 and configured to make the electrode 270b be in close contact with the ganglion cell layer 12 and bipolar cell layer 13.

In the three-dimensional electrode device 100 for stimulating retina prepared as described above, the electrode 120 is in close contact with the ganglion cell layer 12 and the bipolar cell layer 13 and thus can stably apply electrical stimulation to the ganglion cell layer 12 and the bipolar cell layer 13 or measure electrical signals from the ganglion cell layer 12 and the bipolar cell layer 13 at a fixed position.

Further, even if the electrode 120 does not have a pointed end portion, the present invention enables the electrode 120 to be in close contact with the target cells in the retina without damaging the retina because the board 110 and the circuit 130 are formed of flexible materials.

Furthermore, according to the present invention, the board 110 is formed of a transparent material, and, thus, the photo diode 140 is provided to convert light energy into electric energy and the electric energy generated by the photo diode 140 can be provided to the electrode 120 electrically connected thereto. The present invention prepared as described above enables the electrode 120 to stimulate the ganglion cell layer 12 and the bipolar cell layer 13 and measure electrical signals from the ganglion cell layer 12 and the bipolar cell layer 13.

According to the present invention configured as described above, an electrode can stably apply electrical stimulation to the retina or measure an electrical signal from the retina while being in close contact with the target cells to the retina at a fixed position.

Further, according to the present invention, even if the electrode does not have a pointed end portion, the electrode can be in close contact with the target cells in the retina without damaging the retina because a board is formed of a flexible material.

Furthermore, according to the present invention, the board is formed of a transparent material, and, thus, a photo diode is provided to convert light energy into electric energy and electrically connected to the electrode to provide the generated electric energy to the electrode.

The present invention is not limited to the above-mentioned effects, and it should be understood that the present invention includes all effects which can be inferred from the constitutions described in the detailed description or the claims.

While the present invention has been described with respect to the specific embodiments, it will be apparent to those skilled in the art that various changes and modifications may be made without departing from the spirit and scope of the invention as defined in the following claims. Thus, it is clear that the above-described embodiments are illustrative in all aspects and do not limit the present invention. For example, each component described to be of a single type can be implemented in a distributed manner. Likewise, components described to be distributed can be implemented in a combined manner.

The scope of the present invention is defined by the following claims rather than by the detailed description of the embodiment. It shall be understood that all modifications and embodiments conceived from the meaning and scope of the claims and their equivalents are included in the scope of the present invention.

What is claimed is:

1. A three-dimensional electrode device for being implanted in an eyeball, comprising:
    a plurality of pillar structures which are space apart from each other, all of the plurality of pillar structures being made from a same bulk silicon by removal of a part of the bulk silicon;
    a metal layer disposed at a bottom of each of the pillar structures;
    a metal thin film disposed on a top of each of the pillar structures;
    a flexible and transparent material filling between the plurality of pillar structures, height of the flexible and transparent material being lower than height of the pillar structures; and
    a circuit coupled to a lower part of the plurality of pillar structures and the flexible and transparent material, the circuit comprising an array of photo diodes electrically connected to the metal layer at the bottom of the pillar structures,
    wherein when at least a part of the three-dimensional electrode device is inserted into a photoreceptor layer in the eyeball so that the metal thin film on top of the plurality of pillar structures contact a retina, the flexible and transparent material is deformed to correspond to a shape of the retina, thereby allowing the metal thin film on top of the plurality of pillar structures to be in close contact with the retina,
    wherein the photo diodes are located under the flexible and transparent material to allow a light entering into the eyeball to pass through the flexible and transparent material and be received by the photo diodes without being blocked by the plurality of pillar structures, wherein the light received by the photo diodes is converted into electrical energy to stimulate the retina, and
    wherein the metal thin film on top of the plurality of pillar structures have curved surfaces or flat surfaces to be attached to the retina and thus suppress damage to the retina when the metal thin film on top of the plurality of pillar structures are in close contact with target cells in the retina.

2. The three-dimensional electrode device of claim 1, wherein the plurality of pillar structures are arranged in a lattice shape or hexagonal shape or arranged with alternating rows or columns.

3. The three-dimensional electrode device of claim 1, further comprising: an insulating layer covering the three-dimensional electrode device except a surface of the metal thin film on top of the pillar structures.

4. The three-dimensional electrode device of claim 3, wherein the insulating layer is a polymer material including parylene.

5. The three-dimensional electrode device of claim 1, wherein the metal layer at the bottom of the pillar structures are formed of gold (Au) and titanium (Ti) or the gold and chromium (Cr), and the titanium or the chromium enhances an attachment between the gold and the pillar structure formed of silicon.

6. The three-dimensional electrode device of claim 1, wherein the flexible and transparent material is a polymer including polydimethylsiloxane (PDMS) or parylene.

7. The three-dimensional electrode device of claim 1, wherein the plurality of pillar structures are prepared by the removal of the part of the bulk silicon using a deep reactive ion etching or a dicing.

8. The three-dimensional electrode device of claim 1, wherein the plurality of pillar structures are prepared to have curved top surfaces by an isotropic wet etching.

9. The three-dimensional electrode device of claim 1, wherein the metal thin film are formed by depositing a metal thin film material including platinum (Pt) or iridium oxide (IrOx) on end portions of the pillar structures, and the metal thin film are provided to reduce impedance of the pillar structures.

10. A retinal stimulator comprising a three-dimensional electrode device, the three-dimensional electrode device comprising:
    a plurality of pillar structures which are space apart from each other, all of the plurality of pillar structures being made from a same bulk silicon by removal of a part of the bulk silicon;
    a metal layer disposed at a bottom of each of the pillar structures;
    a metal thin film disposed on a top of each of the pillar structures;
    a flexible and transparent material filling between the plurality of pillar structures, height of the flexible and transparent material being lower than height of the pillar structures; and
    a circuit coupled to a lower part of the plurality of pillar structures and the flexible and transparent material, the circuit comprising an array of photo diodes electrically connected to the metal layer at the bottom of the pillar structures,
    wherein when at least a part of the three-dimensional electrode device is inserted into a photoreceptor layer in an eyeball so that the metal thin film on top of the plurality of pillar structures contact a retina, the flexible and transparent material is deformed to correspond to a shape of the retina, thereby allowing the metal thin film on top of the plurality of pillar structures to be in close contact with the retina,
    wherein the photo diodes are located under the flexible and transparent material to allow a light entering into the eyeball to pass through the flexible and transparent material and be received by the photo diodes without being blocked by the plurality of pillar structures,
    wherein the light received by the photo diodes is converted into electrical energy to stimulate the retina, and
    wherein the metal thin film on top of the plurality of pillar structures have curved surfaces or flat surfaces to be attached to the retina and thus suppress damage to the retina when the metal thin film on top of the plurality of pillar structures are in close contact with target cells in the retina.

11. An artificial retina comprising a retinal stimulator which comprises a three-dimensional electrode device, the three-dimensional electrode device comprising:
- a plurality of pillar structures which are space apart from each other, all of the plurality of pillar structures being made from a same bulk silicon by removal of a part of the bulk silicon;
- a metal layer disposed at a bottom of each of the pillar structures;
- a metal thin film disposed on a top of each of the pillar structures;
- a flexible and transparent material filling between the plurality of pillar structures, height of the flexible and transparent material being lower than height of the pillar structures; and
- a circuit coupled to a lower part of the plurality of pillar structures and the flexible and transparent material, the circuit comprising an array of photo diodes electrically connected to the metal layer at the bottom of the pillar structures, wherein when at least a part of the three-dimensional electrode device is inserted into a photoreceptor layer in an eyeball so that the metal thin film on top of the plurality of pillar structures contact a retina, the flexible and transparent material is deformed to correspond to a shape of the retina, thereby allowing the metal thin film on top of the plurality of pillar structures to be in close contact with the retina, wherein the photo diodes are located under the flexible and transparent material to allow a light entering into the eyeball to pass through the flexible and transparent material and be received by the photo diodes without being blocked by the plurality of pillar structures, wherein the light received by the photo diodes is converted into electrical energy to stimulate the retina, and wherein the metal thin film on top of the plurality of pillar structures have curved surfaces or flat surfaces to be attached to the retina and thus suppress damage to the retina when the metal thin film on top of the plurality of pillar structures are in close contact with target cells in the retina.

* * * * *